United States Patent [19]

Simic-Glavaski

[11] Patent Number: 4,855,243
[45] Date of Patent: Aug. 8, 1989

[54] NEUROLOGICAL AND BIOLOGICAL MOLECULAR ELECTRO-OPTICAL DEVICES AND METHODS

[75] Inventor: Branimir Simic-Glavaski, Cleveland Heights, Ohio

[73] Assignee: H.S.G. Venture (a Joint Venture Partnership), Cleveland, Ohio

[21] Appl. No.: 652,317

[22] Filed: Sep. 19, 1984

Related U.S. Application Data

[63] Continuation-in-part of Ser. No. 535,672, Sep. 26, 1983, abandoned.

[51] Int. Cl.[4] ............... G01N 21/64; G01N 21/65; G01N 33/48; G01N 33/68
[52] U.S. Cl. .................. 436/63; 204/157.15; 436/86; 436/89; 436/172; 604/20; 356/301
[58] Field of Search ............... 436/86–90, 436/172, 173, 63; 435/168; 204/157.15, 129; 356/301, 40; 604/6, 20, 24; 422/68; 357/8, 40

[56] References Cited

U.S. PATENT DOCUMENTS

| | | | |
|---|---|---|---|
| 4,305,3909 | 12/1981 | Swartz | 604/24 |
| 3,906,241 | 9/1975 | Thompson | 356/301 |
| 3,999,122 | 12/1976 | Winstel et al. | 436/151 |
| 4,139,348 | 2/1979 | Swartz | 436/35 |
| 4,195,930 | 4/1980 | Delhaye et al. | 356/301 |
| 4,334,880 | 6/1982 | Malmros | 422/68 |
| 4,350,660 | 9/1982 | Robinson et al. | 422/90 |
| 4,428,744 | 1/1984 | Edelson et al. | 604/20 |
| 4,444,892 | 4/1984 | Malmros | 422/68 |
| 4,560,534 | 12/1985 | Kung | 426/68 |

OTHER PUBLICATIONS

Simic–Glaraski et al. J. Electroanal. 150 (1983) 469–479.
Hilaski et al. Nature, vol. 302(7) Apr. 1983.
C.A. 98:194297u; Hilinski et al.
C.A. 99:148324y; Simic-Glaraski et al.

*Primary Examiner*—Michael S. Marcus
*Attorney, Agent, or Firm*—Renner, Otto, Boisselle & Sklar

[57] ABSTRACT

According to one aspect of the invention operationally macrocyclic molecular structures are employed to input and/or to read out information, electrical potential, optical characteristics, energy levels, state information, etc. with respect to another material, such as a neurological or biological material, nucleic acid or other materials. In one example disclosed in the above mentioned application macrocyclic molecules were adsorbed on a silver substrate; in the present invention the operationally macrocyclic molecular structure is adsorbed onto other substrates, such as nerve cells, muscles, nucleic acid (RNA and DNA), etc.

27 Claims, 5 Drawing Sheets

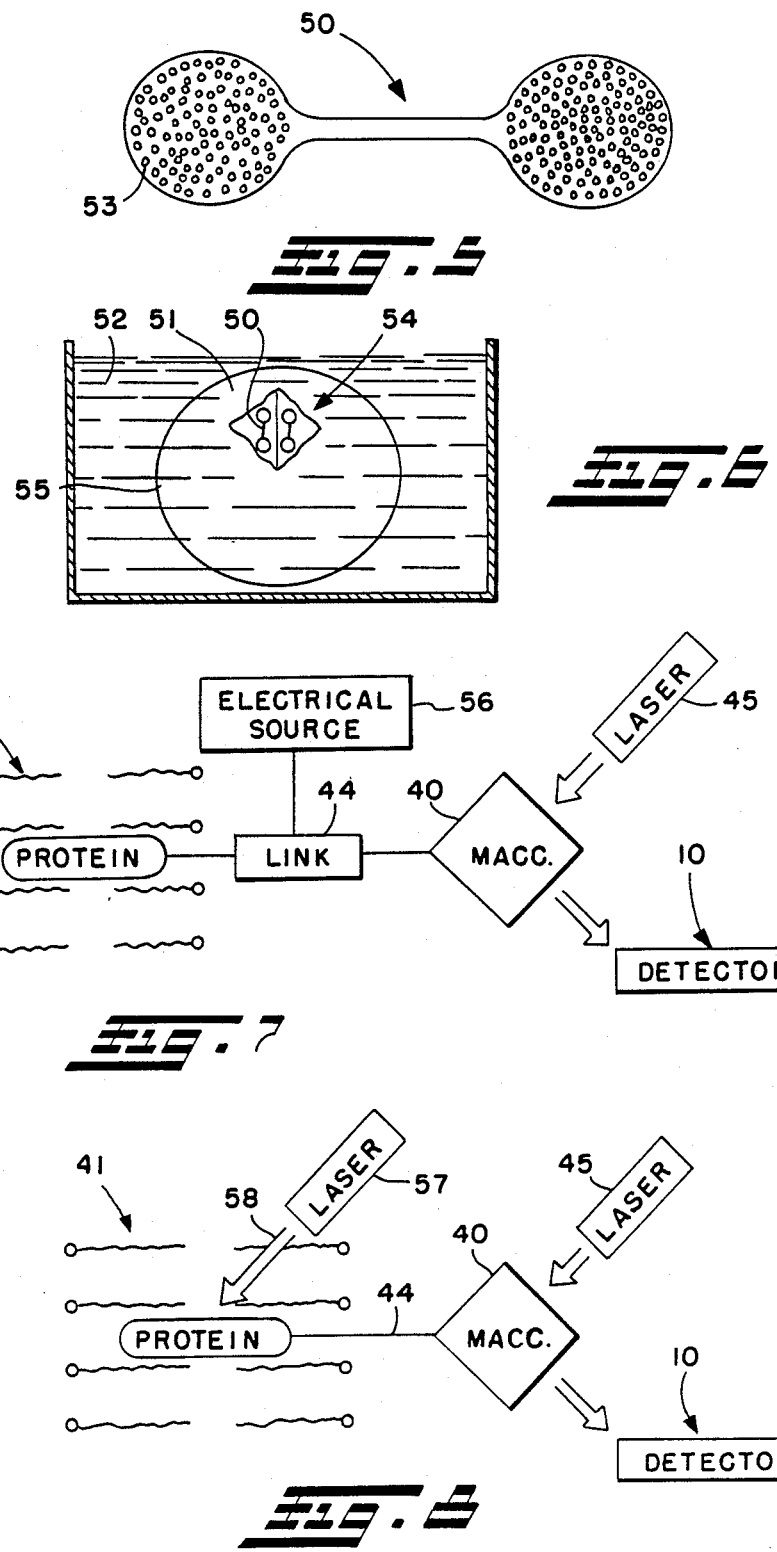

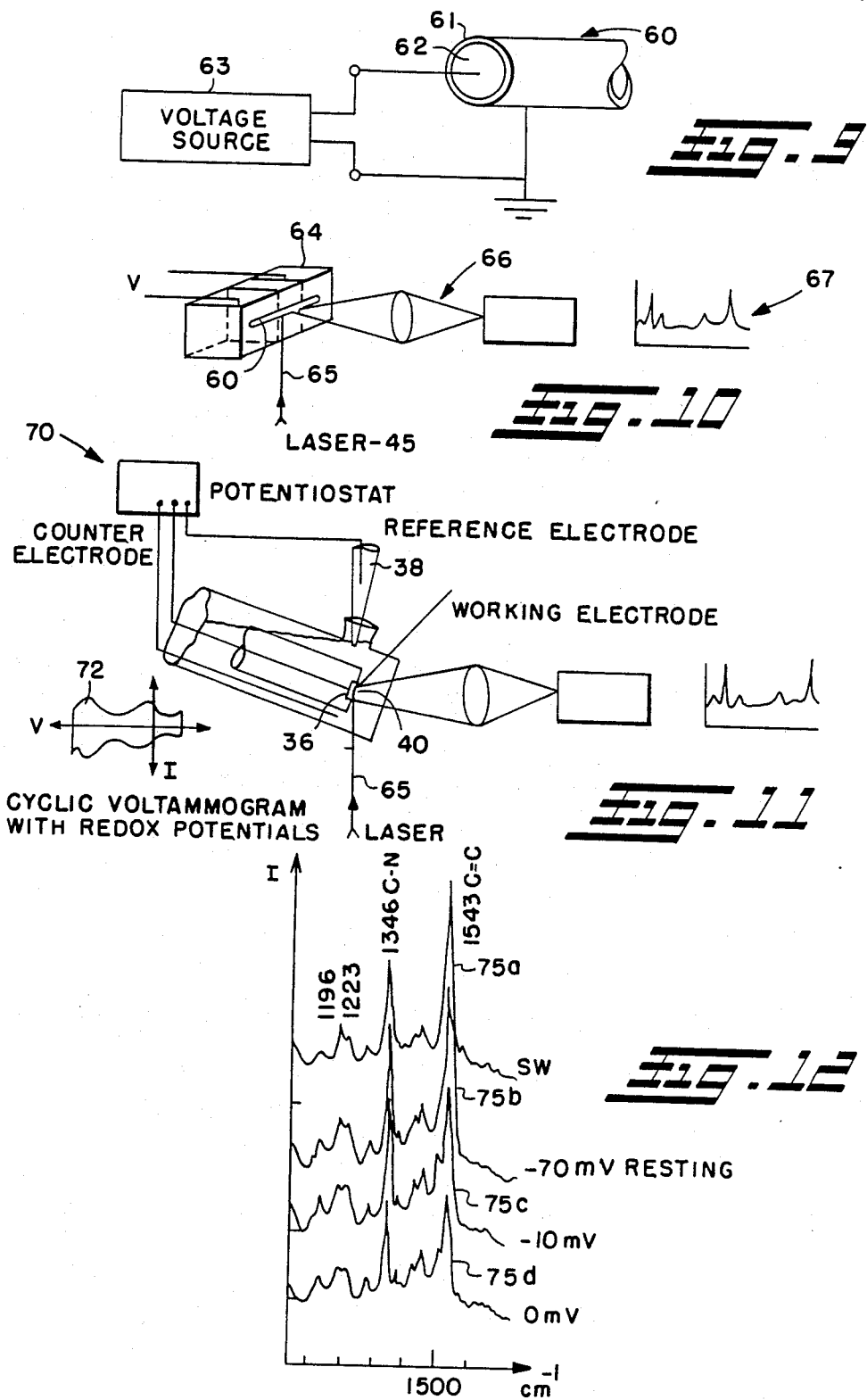

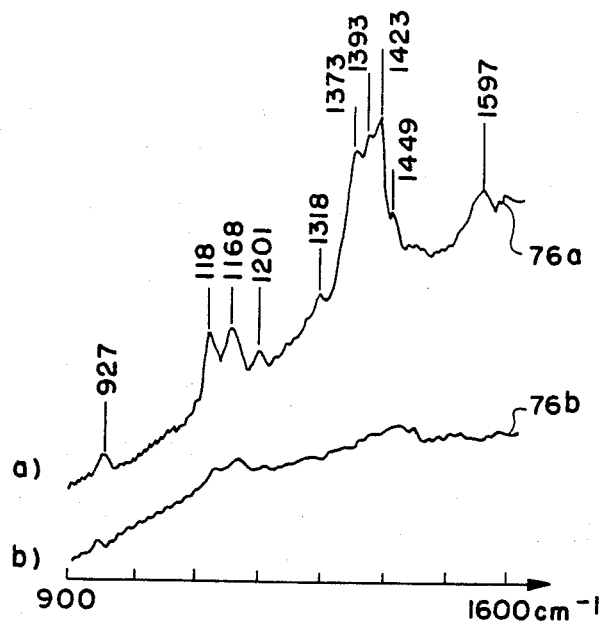
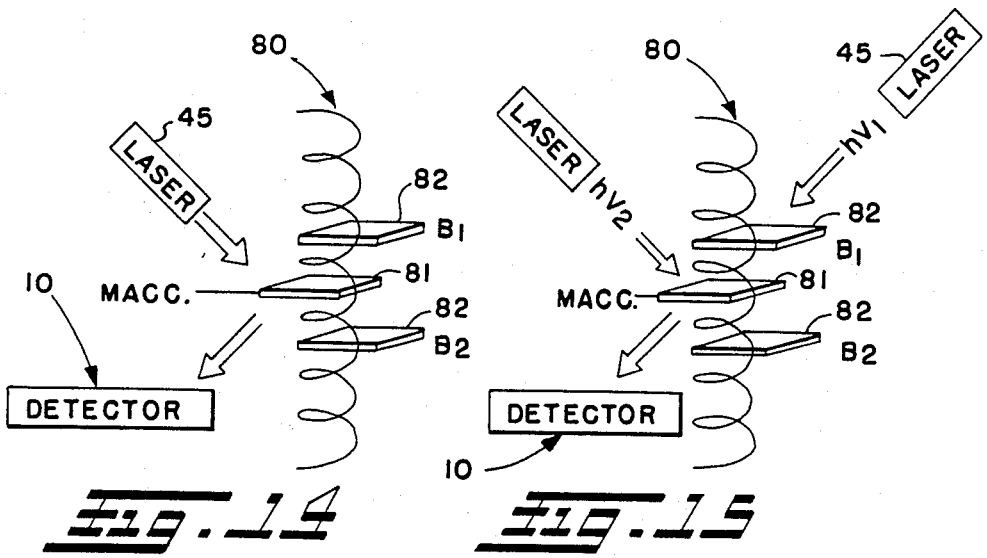
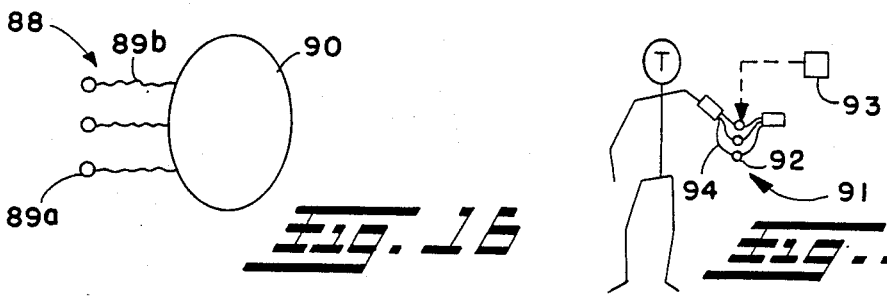
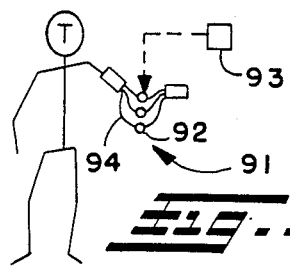

NEUROLOGICAL AND BIOLOGICAL MOLECULAR ELECTRO-OPTICAL DEVICES AND METHODS

CROSS-REFERENCE TO RELATED APPLICATION

This is a continuation-in-part of applicant's copending, commonly assigned, U.S. Patent application Ser. No. 535,672, filed Sept. 26, 1983, and now abandoned, the entire disclosure of which hereby is incorporated by reference.

BACKGROUND

Observable changes in the electrical and optical characteristics of individual molecules adsorbed on a conductor or semi-conductor caused by electrical and/or optical excitation or de-excitation of electrons within such molecules can be used as signals to carry information, as is disclosed in the above-referenced application. Such a molecule or molecules can be observed using optical spectrophotometric methods to obtain a Raman spectrum which reveals the condition or state of energization of a molecule, including, for example, the location of one or more electrons, especially free electrons, therein, the energization level of the molecule and/or electron(s), and the nature of the incident electromagnetic beam, e.g. laser light, used directed to the molecule(s) in the Raman spectrophotometric process. The Raman spectrum so derived for a given condition/energization of the molecule(s) ordinarily will include one or more Raman lines of respective intensities the whole of which may be considered a "fingerprint" of the state of the molecule.

Such molecular devices are characterized by a high speed of response. As is disclosed in such application, switching times may be on the order of $10^{-13}$ second and even to $10^{-15}$ if the molecule exhibits tunnelling.

Dyes have been used in the past to obtain information about the state of nerves. In such case the nerve was stained using methyl orange, and a resonant Raman effect was observed when the dyed nerve was illuminated by a laser line at 488 nm. One problem with such technique is that it is invasive the stained nerve dies or loses its vitality in relatively short time. Another problem is the lack of definition or resolution of the resonant Raman spectrum using such observational methods, e.g. for a lobster nerve stained with methyl orange.

In the medical/technological fields it has been proposed to use nucleic acid molecules, such as RNA and DNA molecules, for the storage of information. The storage capacity of a DNA molecule has been estimated to be between $2^{18}$ to $2^{20}$ bits of information. Satisfactory techniques to input and to read out such information have not heretofore been available.

SUMMARY

According to one aspect of the invention operationally macrocyclic molecular structures are employed to input and/or to read out information, electrical potential, optical characteristics, energy levels, state information, etc. with respect to another material, such as a neurological or biological material, nucleic acid or other materials. In one example disclosed in the above mentioned application macrocyclic molecules were adsorbed on a silver substrate; in the present invention the operationally macrocyclic molecular structure is adsorbed onto other substrates, such as nerve cells, muscles, nucleic acid (RNA and DNA), etc.

As used herein, an "operationally macrocyclic molecule or molecular structure" means a molecule that is a macrocyclic molecule or a molecule that behaves as a macrocyclic molecule to accomplish the functions described in greater detail below. Examples of macrocyclic molecules include phthalocyanine (abbreviated Pc), such as a metal phthalocyanine (one preferred would be iron (abbreviated Fe), cobalt or copper phthalocyanine, which may be sulfonated (one preferred sulfonation would be tetrasulfonated (abbreviated Ts)) or not, porphyrine, chlorophyl, hemes, hemoglobin (a macrocyclic with a protein molecule) and cytochromes. One example of a material (molecule) that is not a macrocyclic but which behaves as a macrocyclic is phytochrome. A phytochrome is a molecule which changes state upon illumination by light, as is the case when such molecules are contained in plants. It is possible to shine light of one frequency on such material to cause the material to become sensitive to light of another frequency. Throughout this application reference to macrocyclic molecule or macrocyclic molecules, then, is to be understood to include operationally macrocyclic molecular structures.

Another aspect of the invention relates to a method for reading out the state of a neurological or biological substance, including linking an operationally macrocyclic molecule with respect to such substance, directing electromagnetic radiation at such molecule, and detecting light scattered by such molecule, whereby such detected light is representative of the state of such substance.

An additional aspect of the invention relates to a method of affecting the state or function of a neurological or biological substance, including linking an operationally macrocyclic molecule directly or indirectly to such substance, and applying at least one of an electrical or optical input to such molecule causing the latter to affect the state of such substance.

A further aspect relates to a method of affecting nucleic acid, including linking an operationally macrocyclic molecule to a molecule of such acid, and applying an electrical or optical input to the operationally macrocyclic molecule to effect a charge transfer or other change of state between the latter and such acid molecule.

Still another aspect relates to a method of reading out the state of at least part of a nucleic acid molecule, including linking such acid molecule with an operationally macrocyclic molecule, applying electromagnetic radiation to such operationally macrocyclic molecule at a wavelength or frequency that does not affect such molecule but is capable of scattering therefrom, and detecting such scattered electromagnetic radiation as a representation of the state of at least part of such nucleic acid molecule.

Still an additional aspect relates to a memory device including a nucleic acid molecule and an operationally macrocyclic molecule linked with respect to the acid molecule to input and/or to read out information with respect to such acid molecule.

Still a further aspect relates to the linking of macrocyclic molecules to the nerves and/or muscles of a living animal and providing stimuli to such macrocyclic molecules thereby artificially simulating a biological or neurological function. Examples may be the use of such devices to detect light or other electromagnetic radiation and the use in artificial limbs utilizing input from non-biological/non-neurological sources or from biological or neurological sources. Another example may be artificial control of natural limbs that have been at least in part otherwise incapacitated from natural operation or function.

Even another aspect relates to a discovery that the energization of macrocyclic and other structures to different quantum levels, so that the energy level of such structures move to different quantum wells, can result in different respective state vector output fingerprints in the resonant spectrum analysis of the structure. This discovery enables utilization of multi-level and multi-output characteristics for a single molecular device with capabilities of very fast switching speeds.

These and other objects and advantages of the present invention will become more apparent as the following description proceeds.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 5 is a schematic illustration of a neural ganglia pair;

FIG. 6 is a schematic illustration of an animal in a physiological solution and exposed ganglia pairs linked to macrocyclic molecules for affecting or for reading out the state of neural cells;

FIG. 7 is a schematic illustration of a macrocyclic molecule linked via an interface material to a nerve and an electrical system and an optical system for affecting and for reading out, respectively, the state of such nerve;

FIG. 8 is a schematic illustration of a macrocyclic molecule linked directly to a nerve, an optical system for reading out the state of the nerve, and a laser system for affecting the state of the nerve;

FIG. 9 is a schematic illustration of a nerve fiber coupled to a variable voltage source for selectively applying different electrical potential to the nerve;

FIG. 10 is a schematic illustration of an optical system, especially of the Raman spectrophotometric type, for examining or reading out the state or other information of a nerve;

FIG. 11 is a schematic illustration of a system similar to that of FIG. 1 for making a controlled examination of a macrocyclic molecule(s) to obtain data for facilitating analysis of data obtained from the nerve in FIG. 10;

FIG. 12 is a graphical representation of the resonant Raman spectra from $10^{-5}$ molar iron tetrasulfonated phthalocyanine (abbreviated Fe-TsPc) in artificial sea water and Fe-TsPc adsorbed on a nerve bundle with various polarization potentials across the membrane in millivolts at a temperature of about 20 degrees C.;

FIG. 13 is a graphical representation of the resonant Raman spectra from $5 \times 10^{-5}$ molar methyl orange in sea water and from a lobster nerve stained by $5 \times 10^{-5}$ molar methyl orange, at resting potential;

FIGS. 14 and 15 are schematic illustrations of macrocyclic molecules used with nucleic acid molecules; and FIGS. 16 and 17 are schematic illustrations of neurological/biological uses of macrocyclic molecules adsorbed on neurological/biological substrates in accordance with respective embodiments of the invention.

DESCRIPTION OF THE PREFERRED EMBODIMENTS

Figure 1:
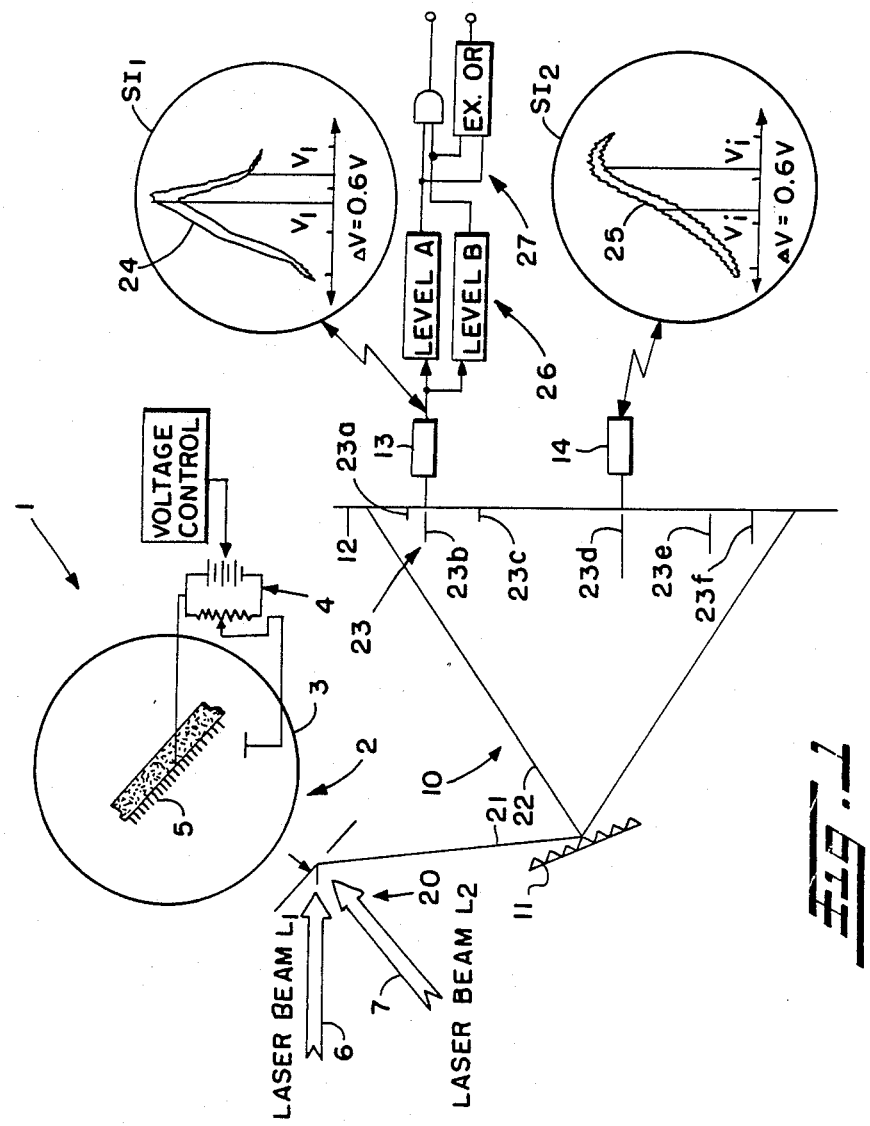
FIG. 1 is a schematic illustration of an electro-optical switch system showing a macrocyclic molecule adsorbed on a substrate with a Raman spectrophotometric detector.

Referring in detail to the drawings, an electro-optical system useful in the invention is indicated at 1. In the system 1 there is a molecular electro-optical device 2, an enlarged illustration of one version of such device 2 in the form of a molecular electro-optical switch 3 being shown, including macrocyclic molecules adsorbed on the surface of a silver electrode. A selectively adjustable variable voltage electrical supply 4 is used to energize, i.e. to apply electric potential, to the macrocyclic molecules 5 of the device 2. One or more laser beams 6, 7 provide an optical input to the device 2 for effecting an energization function, e.g. when the frequency of the laser light or other electromagnetic energy source is such that it affects the macrocyclic molecule, and/or for reading out the state of the macrocyclic molecule.

A Raman spectrophotometer analyzer or detector 10 is the remaining portion of the electro-optical system 1. The analyzer includes a grating 11, which separates light received from the device 2 into its spatially distributed components, which are directed onto a screen 12 or into a plane where they can be observed or electrophotosensitively detected. For the latter purpose the analyzer or detector includes one or more photosensitive detector devices, such as those shown at 13, 14, which may be, for example, photomultipliers, photosensitive diodes, a grid of semiconductor photosensors also made of macrocyclic molecules, etc., for producing an electrical signal or characteristic representing the intensity of light received thereby.

In operation of the system 1, incident illumination 20 is directed onto the device 2. Scattered light 21 from the device is directed to the Raman spectrophotometer detector 10 to analyze the intensity, wavelength, frequency, and/or spatial distribution of the components of the scattered light. The macrocyclic molecules are excitable in response to electrical and/or optical input so as to change from a natural or unperturbed state to an excited one, and the level or extent of such excitation will depend on electrical potential and/or wavelength, frequency and/or intensity of incident light. Such excitation causes an ionization type effect with the result that there appears to be an intermolecular or intramolecular charge transfer, trapping or excitation to an excited state of an electron at a particular location in the molecule(s). The location of such trapping or excited electron may be a function of the input potential and/or light wavelength, frequency and/or intensity and may alter the natural vibrational characteristic of an intramolecular bond. Such alteration changes the optical characteristics of light scattered by the molecule.

Preferably the analyzer 10 is a Raman spectrophotometer to achieve spatial distribution in the frequency domain of scattered light and to measure intensity of each spectral component. The operation of the Raman spectrophotometer may be along the lines of mono-surface enhanced Raman scattering; however other optical analyzers also could be used if capable of detecting the desired information according to the invention.

In the Raman spectrophotometer detector 10 of FIG. 1, the triangular envelope 22 represents the maximum extremities of the spatial distribution of the spectral components of the scattered or re-radiated light 21 from the device 2, as separated by the grating 11 and electrophotosensitively detected. Within that envelope ordinarily would be a number of Raman spectrum lines 23. If the band pass on the monochromator of the spectrophotometer 10 were relatively wide, such as 20 $cm^1$, then the photosensor detector 13 can produce an output volt-Raman graph represented at 24 of intensity versus potential of the macrocyclic molecules. A different volt-Raman graph 25 may be produced by a second photosensor 14 and by other respective photosensos, each of which preferably would be positioned to sense light at a given frequency as separated by the monochromator grating 11.

As is disclosed in detail in the above mentioned application, the electro-optical system 1 as a high speed switch responsive to electric potential applied to the molecules 5, may have a response time from about $2 \times 10^{-13}$ to $5 \times 10^{-13}$ second at room ambient temperature on the order of from about 60-80 degrees F.

Various electronic and other logic schemes may be used to decipher and/or to utilize the output(s) from the system 1. One example illustrated in FIG. 1 includes several logic level discriminators 26, which pass output signals only when the magnitude of the output from the photosensor 13 is above a prescribed level, logic gates 27 for operating logically on the outputs from the discriminators, etc. Analog detecting devices also could be employed, for example to provide an analog output representing intensity of the light at the given Raman spectrum line.

Figure 2:
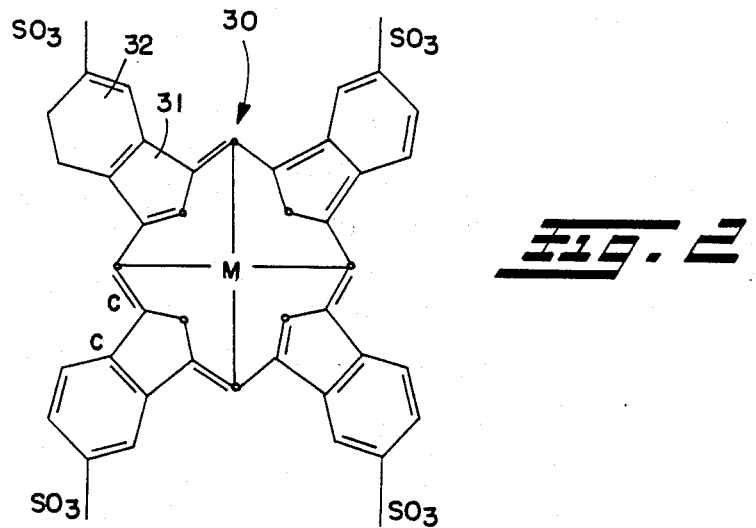
FIG. 2 is a schematic illustration of a macrocyclic molecule in the form of tetrasulfonated phthalocyanine, which may be employed in accordance with the present invention as an adsorbed monolayer on a substrate, such as on a nerve, muscle, or nucleic acid, as well as on a conducting or semiconducting substrate, such as silver or a semiconductor, as is disclosed in the above mentioned application.

An example of a water-soluble TsPc molecule that may be adsorbed on the silver substrate shown in FIG. 1 is represented in FIG. 2. The molecule 30 in FIG. 2 is a tetrasulfonated phthalocyanine (TsPc). The molecule 30 is composed of four pyrrole rings 31 and four benzene rings 32 which form greater inner and outer rings. The inner ring may contain two protons which form a metal-free phthalocyanine ($H_2$-Pc) or may have four coordinated central metal ions which creates a variety of metal-phthalocyanines (M-Pc). Such metal ions are represented by the letter "M" in FIG. 2, and in the preferred embodiment and best mode of the invention are iron (copper and cobalt also are useful). Such phthalocyanines are available commercially from Kodak Corporation, Rochester, New York. Sulfonation appears to have minimal effect on overall molecular characteristics, but sulfonation does enable the other aqueous insoluble Pc molecules to be soluble in aqueous media, which is desirable when water is used as the solvent. For organic solvent use, though, such Pc molecules need only be soluble in such solvent, and, therefore, sulfonation may not be necessary or desired.

Figure 3:
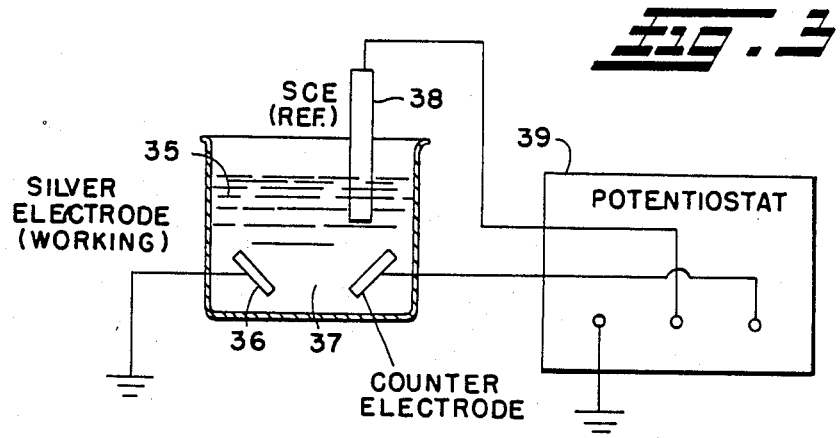
FIG. 3 is a schematic illustration of a system for activating a silver electrode and for adsorbing molecules thereon.

In FIG. 3 is represented a system for activating a silver electrode and adsorbing macrocyclic molecules thereon. Further details are presented in the above mentioned application. Such silver electrode with adsorbed macrocyclics can be used in the present invention, for example, to provide control information for analysis of Raman spectra obtained from neurological and biological substrates. In the system of FIG. 3 macrocyclic molecules (TsPc) 35 were adsorbed to form a monolayer film on the electrode 36. The silver electrode 36 was placed in a chemically clean aqueous bathing medium 37 of a pH 1 and 0.05 molar of sulfuric acid and $10^{-5}$ molar macrocyclic material and was subjected to annodization potential of 500 mv. versus a saturated calomel reference electrode 38 for 30 to 60 seconds. A potentiostat type device 39 was used to provide the electrical input for annodization in the usual potentiostat type of technique. This procedure was used to activate the silver interface and to form an adsorbed monolayer of macrocyclic molecules.

Figure 4:
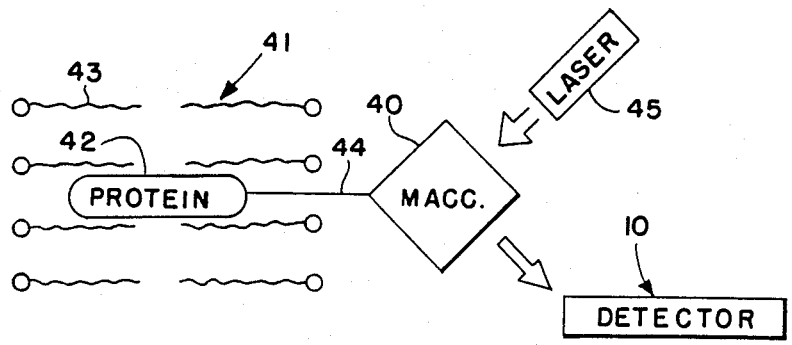
FIG. 4 is a schematic illustration of a macrocyclic molecule linked directly to a nerve and an optical system, such as a Raman spectrophotometer, especially for reading out the state of the nerve.

Turning now to FIG. 4 a macrocyclic molecule 40 is shown linked to a nerve 41. According to a principal aspect of the invention, macrocyclic molecular devices are adsorbed on neurological and/or biological substances, which serve as the substitute substrate for the silver in the aforementioned example of FIG. 3, for example. The nerve 41 is composed of a protein molecule 42 held by lipids 43 as part of the nerve membrane. The link represented at 44 between the nerve and macrocyclic molecule appears to be a physical one which greatly reduces the possibility of a detrimental effect on the nerve by the macrocyclic molecule; and in FIG. 4 such link is shown as a direct link between the macrocyclic molecule(s) (preferably only a single macrocyclic molecule is required) and the nerve membrane. The link, moreover, is such that charge transfer, for example, transfer of one or more electrons or excitation or de-excitation of one or more electrons, can occur between the macrocyclic and the nerve causing a detectable change in the condition of the macrocyclic. Using a laser source 45 of electromagnetic radiation at a frequency or wavelength which is capable of being scattered by the macrocyclic without affecting the macrocyclic and a Raman spectrophotometer detector 10, as above, to detect the scattered radiation, i.e. preferably light, the characteristics, state, etc. of the nerve can be read out. Specifically a resonant Raman spectrum can be obtained to reflect the particular state or other characteristic of the nerve.

Importantly, applicant has discovered a compatibility of the macrocyclic molecules and the neural cells. Such compatibility significantly improves the results of use of the invention with respect to living neurological and biological substances because the macrocyclics tend not to speed the demise of such substances. This advantageous characteristic of the invention is in direct contrast to the use of dyes, such as methyl orange, used heretofore to study neurological and biological substances.

It is noted here, too, that if desired the wavelength or frequency of the incident beam from the laser can be selected to affect the macrocyclic so as to cause a charge transfer that would in turn affect the state or condition of the nerve. In this way the macrocyclic could be used as an input device to the nerve. Moreover, it is noted that detailed description herein refers to the linking of macrocyclics with respect to nerves; but it will be apreciated that such linking also may be with respect to muscles and/or with respect to other neurological and/or biological substances. Thus, the macrocyclic molecules, in accordance with the present invention, provide a linking with an optical system for read out and/or for input purposes with respect to a neorological or biological substance.

Represented in FIG. 5 is a ganglia pair 50 from the brain of an animal, such as a sea slug or gastropod 51, which is shown schematically in FIG. 6 immersed in a physiological liquid 52 or artificial sea water. In the ganglia pair 50 are a plurality of neural cells 53. In the past to monitor the activity in a given cell 53 or to provide an externally derived stimulus directly thereto, it was necessary to attach an electrical probe thereto; accordingly very many such probes were needed to monitor a corresponding number of neural cells. Available space for such probes was limited according to the very small size of the ganglia pair and of the neural cells therein, which impaired experimental procedure and impeded progress. Probes also tend to have a deleterious, even destructive, effect on the cells.

According to the present invention, then, macrocyclic molecules can be linked non-destructively and non-invasively with respect to neural, neurological or biological, cells directly to read out or to input information with respect to the same.

EXAMPLE 1

Incubation or staining of neural cells in ganglia pairs of a gastropod 51 would be carried out by cutting the tissue of the gastropod at 54 to expose ganglia 50, i.e. neural cells. A solution of $10^{-4}$ to $10^{-6}$ molar macrocyclics in physiological solution (artificial sea water) would be formed using iron phthalocyanine. The gastropod would be immersed in such solution with the ganglia exposed.

EXAMPLE 2

Behavior analysis and modification of the gastropod would be possible using the neural cells with linked macrocyclics. Specifically, the gastropod 51 would be given an external, non-neural, stimulus; food would be placed in proximity to the gastropod which would sense the same (beer and squid would be particularly useful) and that sensing would cause the gastropod to open its mouth 55. Immediately upon encountering such opening, a negative stimulus, one which tended apparently to induce a discomfort in the gastropod, would be applied to one or more neural cells at the exposed ganglia by the application of an input to the linked macrocyclic molecule(s) there. After several, usually less than ten, repetitions, the gastropod would learn new behavior and would not open its mouth in response to the food stimulus.

Using the above approach, the state of the neural cells could be read out, for example, in the manner illustrated in FIG. 4, during the stimulation experiments, as food is placed near and removed from the gastropod.

As is seen in FIG. 7, an interface material 44' may be employed to link the macrocyclic molecule with the nerve membrane or cell. Such interface material provides a medium to apply electrical stimulus from a controllable electrical source 56 and the nerve 41. For this purpose, it is desirable that the link interface be of a semiconductor type of material; examples include polydiacetylene, polypyrroles and doped lipids. Another link interface material 44' may be rhodopsin, which is a light sensitive material capable of responding to an optical stimulus to input an electrical stimulus to the nerve 41. The system of FIG. 7 operationally is the same as the system in FIG. 4, except for the added dimension that the electrical source 56 permits direct application of electrical stimulus to the nerve 41 while the macrocyclic molecule provides for a read out of information using the non-affecting laser 45 and the Raman spectrophotometric detector 10.

Another embodiment of the invention is illustrated in FIG. 8. There a nerve 41 is linked with respect to a macrocyclic molecule 40, and a laser 45 and Raman spectrophotometric detector 10 are used to read out the state of the nerve substance. However, in FIG. 8 a laser 57 provides a source of electromagnetic radiation 58 incident on the nerve to affect the state or energization level thereof; the wavelength/frequency of such radiation is selected to have such effect. The macrocyclic 40, laser 45 and detector 10 are used to read out the state of such nerve as such excitation by laser 57 is carried out. If desired, though, the link interface 44' and the electrical source 56 excitation also may be employed in the embodiment of FIG. 8.

In view of the foregoing it will be appreciated that various techniques may be employed to input and/or to read out information and excitation with respect to neurological and biological substances using macrocyclic molecules, especially with Raman spectrophotometry detector systems. Examples of methods and apparatus for carrying out such techniques now are described in further detail with respect to FIGS. 9-12.

Represented in FIG. 9 is a nerve fiber 60 having an outer membrane 61 and an interior 62. As is known, the nervous systems of lobsters and of human beings have similar characteristics, one of which is the natural tendency of the nerve to have an electrical potential drop of $-70$ mv. between the outer membrane 61, which is at relative ground potential, and the interior 62. This potential of $-70$ mv. is usually known as the resting potential of the nerve. A voltage source 63 in FIG. 9 is selectively adjustable or settable to apply different electrical potentials to the nerve 60; an example being from the rest state of $-70$ mv., i.e. the source 63 having no effect, to 0 mv. The result on the Raman spectra for such nerve as analyzed according to the invention is shown graphically in FIG. 12, and the apparatus for making the analysis is schematically illustrated in FIG. 10.

More particularly, the nerve fiber 60, which had been incubated or otherwise linked with respective macrocyclic molecular structure, was supported and contained in a supporting container 64 shown in FIG. 10 in electrical isolation from the container walls, e.g. using Vaseline petroleum jelly as the electrical insulating material. Laser light 65 from a laser 45 was directed to the nerve 60, and light scattered from the nerve was analyzed by a Raman spectrophotometric detector 10, including appropriate lenses 66, monochromator 11, and photosensitive detector(s) 13. A schematic graph 67 in FIG. 10 shows the type of resonant Raman spectrum obtained from a detection of scattered light from the nerve 60 at a given potential.

To obtain information on the nature of the macrocyclic molecules used in the analysis of the nerve 60 and the reaction thereof with respect to different electrical potentials, the apparatus 70 of FIG. 11 was used. The apparatus 70 is similar to the apparatus of FIGS. 1 and 3 in that a silver substrate 36 having a monolayer of macrocyclic molecules 40 is illuminated by laser light 65' from a laser source 45. Different resonant Raman spectra are measured and graphed, as at 71, at different respective potential values of the working electrode (silver substrate with macrocyclic monolayer) with respect to a reference electrode 38 (which may be a saturated calumel electrode). Further a cyclic voltammetry curve 72 is developed as such potential is varied and as the resonant Raman spectra are obtained; such cyclic voltammetry curve may be used for reference purposes when data is taken and/or is analyzed for the nerve 60. In FIG. 12, the top curve 75a shows the resulting Raman spectrum for such sea water measured using the apparatus of FIG. 11.

The remaining three curves of FIG. 12 designated 75b, 75c, and 75d are the resonant Raman spectra of the nerve 60 measured using the apparatus of FIG. 10 at the rest potential —70 mv., potential of —10 mv. and 0 mv. The differences in the curves can be compared to provide information about the state and energization level of the nerve. It is noted that the Raman line at 1543 $cm^{-1}$ represents vibration of a cabon-carbon bond; and the line at 1346 $cm^{-1}$ represents vibration of a carbon-nitrogen bond. Thus, it will be appreciated that during changes in energization potential with respect to the nerve 60 a charge transfer occurs between the nerve and the macrocyclic molecule(s) linked thereto; and the result of such charge transfer can be optically read out using the Raman spectrophotometric techniques employed according to the invention.

The foregoing is in contrast to the result achieved in the past using various dyes to stain neurological substances. For example, as is shown in FIG. 13, curve 76a represents resonant Raman spectrum for $5 \times 10^{-5}$ molar methyl orange in sea water. However, curve 76b in FIG. 13 represents the Raman spectrum from a lobster nerve stained by $5 \times 10^{-5}$ molar methyl orange for fifteen minutes and then washed several times by clear sea water. Recording at the nerve resting potential with laser excitation at 100 mw. at 488 nm and resolution 2 $cm^{-1}$. The lack of resolution of the Raman lines in curve 76b relative to the resolution or distinctiveness of the lines in the curves 76a and those designated 75 in FIG. 12 are significant and demonstrates the substantial advantage of the present invention over prior techniques of neurological analysis.

Since each resonant Raman spectrum for a given substrate and adsorbed macrocyclic molecule may produce multiple outputs, $r_{1max}, r_{2max}, \ldots, r_{imax}$, each representing a different Raman spectrum line, the invention may be said to result in a multi-output system.

It has been noticed in the field of quantum mechanics that various substances may fall into one or more energy wells of relatively lowest free energy level. For example, applicant has noted that macrocyclic molecules may have six separate energy wells or quantum wells or states that the molecule may be force into or which may occur naturally. Applicant also has discovered that for each such energy well, the resonant Raman spectrum may be different from the resonant Raman spectrum at other energy well values. Such states are expressed physically by the position of the free electron(s) in a given macrocyclic molecule. Such states also may be expressed by state vectors in which each vector N has a plurality of 4 values, each representing a different Raman line, for example, and each of which can go from an intensity of zero (0) to a maximum intensity ($r_{max}$) when illuminated with laser light, for example, is initiated in the manner described above.

Thus, for a given energy well or quantum well of a given material having adsorbed macrocyclic molecule(s), the state vector N may be represented:

$$N \begin{pmatrix} (0 - r_{1max}) \\ (0 - r_{2max}) \\ (0 - r_{3max}) \\ \ldots \\ \ldots \\ \ldots \\ (0 - r_{imax}) \end{pmatrix}$$

That each rmax value may be different from the other rmax values in a given state vector, i.e. when the adsorbed molecules and substrate are in a given quantum or energy well, implies that the system can produce multilevel outputs—i.e. a multilevel output system. Such multilevel outputs may be used for analysis purposes or may be used for logic, mathematical, electronic, computer, and like purposes. Exemplary decoding circuitry for converting the optical information, such as that shown schematically in FIG. 1, may be used to derive electrical signals representative of the multilevel outputs of the given Raman spectrum, for example.

However, applicant also has discovered that the different energy well or quantum well conditions of a given substrate and linked macrocyclic molecule(s) can produce different respective state vectors. Thus, the rimax for one state vector may not be the same as rimax for a different state vector, and this result is known as multiple state output capability of a system employing the invention adding a still further dimension to the informational magnitude, quantity, and significance that can be obtained using the invention as well as the outputs, e.g. for memory usage in computer and like technology achievable using the invention.

Mathematically the multiple state output capability of the invention can be represented by the state vector equations, as follows:

$$N_1 \begin{pmatrix} (0 - r_1) \\ (0 - r_2) \\ (0 - r_3) \\ \ldots \\ \ldots \\ (0 - r_i) \end{pmatrix} \neq N_2 \begin{pmatrix} (0 - r_1) \ldots \\ (0 - r_2) \ldots \\ (0 - r_3) \ldots \\ \\ (0 - r_i) \ldots \end{pmatrix} \neq N_n \begin{pmatrix} (0 - r_1) \\ (0 - r_2) \\ (0 - r_3) \\ \\ \\ (0 - r_i) \end{pmatrix}$$

The peaks on the cyclic voltammogram 72 in FIG. 11 represent those portions of an adsorbed macrocyclic monolayer on a silver substrate where energy wells will occur. Energy wells of different values may be forced on the macrocyclic and substrate by applying a given potential to the substrate, e.g. the one demonstrated in FIG. 11. Likewise, different energy wells can be forced in other biological and neurological substances to accomplish the result of analysis and/or input functions.

Briefly referring to FIGS. 14 and 15, a nucleic acid molecule 80, e.g. DNA, is in the form of a helix having many base molecules constituting the same. According to the invention, a macrocyclic molecule 81 may be intercolated between a pair of bases 82, 83 of the molecule 80 to read out the state of the acid molecule or, if desired, to affect the state of the acid molecule. For read out purposes, laser 45 directs light onto the macrocyclic, and the detector 10 analyzes the result. The frequency/wavelength of the laser light should not affect either the macrocyclic or the acid molecule. If desired, though, the light from laser 45 may affect the macrocyclic causing the latter to effect a conformational change, i.e. a charge transfer result, with respect to the acid molecule to affect the latter in a known or unknown way, e.g. for research purposes.

In FIG. 15 the laser 45 directs light of one wavelength onto the macrocyclic 81 to read out state or other information, and another laser 84 which is of a frequency that affects the acid molecule is incident on the latter. According to whether or not the laser 84 is operating and the wavelength, frequency and/or intensity of light or other electromagnetic radiation output thereby, there will be a corresponding detectable result in the macrocyclic.

In view of the complexity of the nucleic acid molecules or similar molecules it will be appreciated that the same may be employed as memory devices, e.g. for computers or other purposes, to store enormous amounts of information in very small space. Such storage may be in the form of quantum well values and resulting state vectors, in untwisting of the nucleic acid molecules and possibly in other ways, as well.

Briefly referring to FIGS. 16 and 17, the same show schematically use of the invention in connection with artificial light sensors for human beings, for example, and artificial limb or disabled limb control. For example, in the device 88 of FIG. 16, there are plural macrocyclic molecules positioned to sense input light, and such macrocyclics 89a are coupled to nerves 89b to affect the latter. The nerves may carry signals to a decoder, whether of the computer or other type, even a device 90 that may be or may interface with an animal, e.g. a human, brain, to provide information about incident light. In FIG. 17 the device 91 can provide information to muscles or to nerves that in turn are coupled to control muscles or artificial devices that effect operation of a limb. Input to the macrocyclic molecules 92 associated with the device 91 may be from an external source, such as a computer 93 (either electrical or optical inputs being provided, since the macrocyclics would result to either type input), or may be from a natural source 94, such as another nerve, a neural cell, a muscle, etc.

STATEMENT OF INDUSTRIAL APPLICATION

It will be appreciated that the invention may be used to read out information from and to input information to neorological and biological substances for a variety of purposes, may be used for artificial limb or disabled limb control, and may be used for information storage and retrieval purposes. The invention also may be used for diagnosis type testing of neurological and/or biological substances and of the effect of drugs, pharmaceuticals and/or other intrusions on neurological and/or biological substances.

I claim:

1. A method of affecting the energy state or function of a neurological or biological substance, wherein such substance is at least one of a nerve or muscle, comprising linking an operationally macrocyclic molecule with respect to such substance so as to be non-destructively and non-invasively linked with respect to such neurological or biological substance, and applying at least one of an electrical or optical input to such molecule causing the latter to affect the energy state of such nerve or muscle.

2. The method of claim 1 said applying comprising illuminating such molecule using laser radiation.

3. The method of claim 1, said linking comprising physically connecting an interface between such molecule and such substance.

4. The method of claim 3, wherein said physically connecting comprises using a semiconductor material as such interface.

5. The method of claim 1, further comprising reading out the energy state of such nerve or muscle.

6. The method of claim 5, such molecule being responsive to the energy state of such substance whereby the energy state of such molecule physically represents the energy state of such substance.

7. The method of claim 6, such substance effecting a charge transfer in the form of one or more electrons or electron energy levels in response to specified state thereof, said reading out comprising directing electromagnetic radiation at such molecule, and detecting light scattered by such molecule as an indication of the energy state of such neurological or biological substance, whereby such detected light is representative of the energy state of such substance, and such molecule receiving such charge transfer and affecting incident light as a function of receiving an electron and the location of such electron with respect to such molecule.

8. The method of claim 5, said reading out comprising directing radiation at a frequency and wavelength that does not affect such molecule.

9. The method of claim 5, said reading out comprising using Raman spectrophotometry.

10. The method of claim 1, further comprising inducing an energy state in such substance.

11. The method of claim 10, said inducing comprising optically illuminating such molecule whereby such molecule effects a charge transfer with respect to such substance.

12. The method of claim 11, said inducing comprising applying an electrical input to such molecule.

13. The method of claim 12, further comprising connecting an electrical conductor or semiconductor material as an interface link physically between such molecule and such substance.

14. The method of claim 13, wherein such electrical conductor or semi-conductor material is selected from the group consisting of polydiacetylene, polypyrroles and doped lipids.

15. The method of claim 13, wherein such electrical conductor or semi-conductor material is a compatible conducting polymer.

16. The method of claim 13, wherein such electrical conductor or semi-conductor material is a semiconductor.

17. The method of claim 13, 14, 15, or 16, said applying comprising applying such electrical input to such interface link.

18. The method of claim 1, wherein such molecule gives up at least one electron to such substance in response to such input.

19. The method of claim 1, said step of linking comprising placing the substance in a liquid containing a plurality of such molecules.

20. The method of claim 19, said placing comprising placing such substance in an electrolyte.

21. The method of claim 20, said placing comprising placing in sea water or artificial sea water.

22. The method of claim 1, said linking comprising placing said substance in a physiological solution containing from about $10^{-4}$ to about $10^{-6}$ molar solution of such molecules.

23. The method of claim 22, such molecule comprising iron phthalocyanine.

24. The method of claim 22, wherein such molecule is selected from the group substantially consisting of cytochromes, chlorophyl, and phytochromes.

25. The method of claim 1, wherein such linking is non-chemical interaction and does not form a chemical complex.

26. The method of claim 1, wherein such linking does not change the molecule or the substance.

27. Apparatus for affecting the state or function of a nerve or muscle substance, comprising an operationally macrocyclic molecule, linking means for linking said operationally macrocyclic molecule with respect to such substance so as to be non-destructively and non-invasively linked with respect to such substance, and applying means for applying at least one of an electrical or optical input to such molecule causing the latter to affect the state of such substance.

* * * * *